United States Patent [19]

Atkinson et al.

[11] Patent Number: 4,780,412
[45] Date of Patent: Oct. 25, 1988

[54] FIBRINOLYTIC ENZYMES PRODUCED FROM ESTABLISHED NON-CANCEROUS CELL LINES

[75] Inventors: Anthony Atkinson; Asgar Electricwala; John B. Griffiths, all of Salisbury; Amy Latter; Patrick A. Riley, both of London; Peter M. Sutton, Salisbury, all of United Kingdom

[73] Assignee: Public Health Lab Svc Bd. University Coll., London, England

[21] Appl. No.: 557,140

[22] PCT Filed: Mar. 4, 1983

[86] PCT No.: PCT/GB83/00067
§ 371 Date: Nov. 4, 1983
§ 102(e) Date: Nov. 4, 1983

[87] PCT Pub. No.: WO83/03101
PCT Pub. Date: Sep. 15, 1983

[30] Foreign Application Priority Data

Mar. 5, 1982 [GB] United Kingdom ............... 8206576

[51] Int. Cl.$^4$ ............................................. C12P 21/00
[52] U.S. Cl. ..................................... 435/68; 435/212; 435/217; 435/240.1
[58] Field of Search ......................... 435/68, 240, 241

[56] References Cited

U.S. PATENT DOCUMENTS 4,317,882  3/1982  Horiguchi et al. ................ 435/240
4,505,893  3/1985  Mori et al. ........................ 435/241
4,537,852  8/1985  Sugimoto ......................... 435/241

OTHER PUBLICATIONS

Wilson et al.—Cancer Research—vol. 40(3) (1980) pp. 933–938.
Smith et al.—J. Supramolecular Structure, vol. 11 (1979) pp. 147–151, 155–161 and 164–166.
Yang et al.—J. Cell Biology, vol. 84 (Jan. 1980) pp. 120–130.
Yang, N. S. et al., "Absence of Fibronictin and Presence of Plasminogen" Biol. Abs. 69, Abstract 51892 (1980).
G. H. Barlow, Chemical Abstracts, vol. 89: 57188j (1978) 1–6, 10–15.
Boyd, J. B., Chemical Abstracts, vol. 90: 52838g, 1–4, 10, 11, 14.
Smith, H. S. et al., Properties of Epithelial Cells Cultured from Human Carcinomas and Nonmalignant Tissues, See Abstract 144655q.
EP, A. 0041766 (Leuven Research and Development (V.Z.W.) Dec. 16, 1981, See Example 1; Claims 6–8.

Primary Examiner—Sam Rosen
Attorney, Agent, or Firm—Browdy and Neimark

[57] ABSTRACT

Fibrinolytic enzymes are produced and then isolated from non-cancerous established cell lines, designated as BEB or GPK. These fibrinolytic enzymes differ from those produced by malignant cell lines.

4 Claims, 5 Drawing Sheets

FIG.1. ZINC CHELATE-AGAROSE CHROMATOGRAPHY

FIG. 2: CONCANAVALIN A-AGAROSE CHROMATOGRAPHY

FIG.4

FIG.5

FIBRINOLYTIC ENZYMES PRODUCED FROM ESTABLISHED NON-CANCEROUS CELL LINES

INTRODUCTION

This invention relates to new fibrinolytic enzymes, methods for their production and pharmaceutical compositions containing them.

Thrombotic vascular occlusion, usually of vessels with long-standing damage to their walls, is the main cause of mortality in the United Kingdom, accounting for at least 2 out of 5 of all deaths. In this group of diseases, coronary artery thrombosis alone kills as many people as all the forms of cancer added together. No comparable figures exist for the morbidity attributable to thrombotic disease (in terms of patients hospitalised, or sick at home) but the numbers must be enormous. A similar situation exists in Western Europe and North America and an article in "Time" magazine reported that cardiovascular disease accounts for one half of all deaths recorded annually in the U.S.A. (Time, June 1, 1981, 43.).

There is, therefore, a great need for effective treatments for these common disorders. It is however, symptomatic of the paucity of drug therapy in this field, that surgery plays a large part in current medical practice, as witnessed by the phenomenal rise in the number of coronary artery by-pass operations performed in America. Up to now (apart from such non-specific treatment as digitalis for the failing ischaemic heart) anticoagulants have been the most widely used type of medication. However, at best, anticoagulants can only inhibit further thrombosis, and the combination of possible haemorrhagic complications coupled with equivocal results in properly controlled clinical trials, has inhibited their more widespread use, except in a few clearly defined situations (e.g. low dosage heparin as a method of reducing the incidence of deep venous thrombosis after surgery).

The most rational medical treatment, in theory, must be to selectively dissolve the offending blood clot. In the test-tube many proteolytic enzymes will lyse coagulated blood, but these enzymes, for example trypsin, would also break down many other blood proteins, and be rapidly fatal (a state of affairs sometimes seen in fulminating acute haemorrhagic pancreatitis). What is needed is an enzyme with a high degree of specificity for fibrin, and only minimal general proteolytic activity. In the body, the naturally occurring enzyme plasmin has these properties.

In the blood stream plasmin normally exists as its inactive precursor, plasminogen. Blood clot is lysed by the plasminogen already trapped in the thrombus being activated to plasmin by substances released from the adjacent damaged vessel wall and which are known as vascular plasminogen activators. In this way, non-fatal blood clots in vessels become gradually recanalised, though the process is slow and inefficient, often taking months or years. It is thus apparent that the use of plasminogen activitors suitable for administration to patients, could be a method of treating thrombotic vascular occlusions.

In 1933, Tillet discovered that an exotoxin obtained from cultures of haemolytic streptococci, was a powerful plasminogen activator; this he called streptokinase (SK). It has never achieved general clinical acceptance for use as a fibrinolytic agent because (a) it is strongly antigenic (as would be expected of a bacterial exotoxin), and thus frequent pyrogenic reactions, and occasional instances of anaphylactic shock, have been reported, and (b) its administration is associated with a considerable risk of generalised bleeding, because SK activates both circulating plasminogen as well as clot-bound plasminogen, and the former causes widespread destruction of several of the normal blood coagulation factors, viz. Factor I (fibrinogen), Factor II (prothrombin), Factor V (labile factor) and Factor VIII (anti-haemophilic globulin).

A decade later, another plasminogen activator was found in normal human urine, and named Urokinase (UK). This is far less (if at all) antigenic, but it, too, is associated with activation of plasminogen in the blood, and hence carries a similar risk of severe haemorrhage, which restricts its clinical usefulness.

It has been suspected for many years that tissues other than blood vessels contain plasminogen activitors. These are collectively termed "tissue activators", but far less is known about tissue activators than about streptokinase and urokinase. It may be that tissue activators are chemically a diverse group of substances, united only by their ability to convert plasminogen into plasmin. However, most workers believe that all tissue activators arise from the blood vessels of the tissues in which they are found (i.e. from vascular endothelium) and hence are identical with vascular plasminogen activator, which has a molecular weight of 72,000. It is further claimed that other tissues acquire a plasminogen activator if they become cancerous, and that this accounts for some of the invasive properties of malignant cells.

A newly discovered tissue activator (referred to as Human Extrinsic Plasminogen Activator-HEPA) has been the subject of a recent series of publications. This tissue activator is secreted by a line of human (malignant) melanoma cells, and it also has a molecular weight of 72,000 daltons. In the presence of reducing agents it is split into two subunits of 39,000 and 33,000 daltons. This tissue activator has been tested both experimentally (in rabbits) and on two patients, but the cancerous origin of the substance must limit its use clinically since it is clearly unsatisfactory to use as a therapeutic agent, a substance which has been derived from malignant cells. In fact, the two human patients on whom this tissue activator was tested were desperately ill, and would almost certainly have died without treatment. Nevertheless, HEPA (both clinically and experimentally) has been shown to be a more effective and far safer clot lyser than urokinase. This is because HEPA selectively activates plasminogen bound to thrombus, and spares the circulating plasminogen.

An article entitled "Absence of Fibronectin and Presence of Plasminogen Activator in both Normal and Malignant Epithelial Cells in Culture" by N.-S. Yang et al (J. Cell Biology 84 (1980), pages 120–130), describes the presence of plasminogen activator in cultures of human epithelial cells which are either primary or early passage cultures or malignant.

An article entitled "Properties of Epithelial Cells Cultured from Human Carcinomas and Non-Malignant Tissues" by H. S. Smith et al (J. Supramolecular Structure 11 (1979), pages 147–166) also describes the production by malignant or primary epithelial cell cultures of plasminogen activator.

It has now been discovered that certain established epithelial cell lines are capable of producing in tissue culture, enzymes which are active as plasminogen activators. Also an enzyme from one cell line at least has been found to possess fibrinolytic activity per se, that is to say the enzyme itself is active in lysing fibrin in the absence of plasminogen.

According to one aspect of the present invention there is provided a method of producing an enzyme having fibrinolytic activity per se and/or activity as a plasminogen activator which comprises culturing cells of the established epithelial cell line designated GPK (CNCMI-222) or cells of the established epithelial cell line designated BEB (CNCMI-221) and isolating an enzyme-containing fraction from the culture characterized in that the epithelial cells are an established cell line. The enzyme-containing fraction may either be obtained by collecting a supernatant fraction containing the enzyme or the enzyme-containing fraction may be extracted from the cells.

In producing enzyme in accordance with the invention, the chosen cells may be grown in serial culture by normal tissue culture techniques, for example in a serum-containing medium. Once an adequate proliferation of cells has been achieved, the serum-containing medium may be replaced by a serum-free medium. The cells may then be maintained under physiologically appropriate conditions until an adequate production of enzyme has taken place and the enzyme may then be recovered from the supernatant, or by direct extraction from the cells.

Any appropriate recovery technique may be utilized, but preferably the enzyme is recovered from pooled aliquots of supernatant by centrifuging to remove any suspended cells, followed by metal chelate, ion exchange and/or exclusion chromatography. Fractions containing proteins may be identified by measuring the U.V. absorbance at 280 nm and assaying the protein-containing fractions for fibrinolytic and/or plasminogen activating activity by fibrin plate method and/or fibrin clot lysis time method.

Enzymes have been isolated according to the invention from the aforesaid established cell lines which have a molecular weight as determined by sodium dodecyl sulphate polyacrylamide gel electrophoresis (SDS-PAGE), under reducing conditions, of $62,000 \pm 3000$ daltons, a molecular weight under non-reducing conditions of approximately $56,000$ daltons $\pm 2000$ and an isoelectric point of 4.6. The enzymes have amino acid analyses substantially as shown in Table 3.

These enzymes are believed to be novel and form a further aspect of the invention as does the isolation of these enzymes by the methods described above, and pharmaceutical compositions comprising the enzymes and a pharmaceutically acceptable diluent or carrier. The choice of carrier will depend on the intended route of administration and for parenteral administration a suitable carrier is sterile pyrogen-free normal saline. The enzymes may also be administered orally and conventional excipients for oral use may be employed. Clinical indications for use of the enzymes of the invention include the diagnosis, prevention and treatment of venous thromboses (including deep vein and retinal thromboses), pulmonary emboli, intracardiac clotting, arterial thromboemboli, microvascular thromboemboli, inflammatory exudatory conditions and the presence of blood in body cavities, as in haemothorax.

One cell line referred to above is maintained in a culture collection at University College, London under the reference GPK and the other cell line of human breast epithelium is maintained in a culture collection at University College, London under the reference BEB; and both have been deposited at the (internationally recognised) Collection Nationale de Cultures de Microorganismes at the Institut Pasteur, on Feb. 25, 1983, Accession Numbers I 221 for BEB and I 222 for GPK.

By contrast with the previously described human extrinsic plasminogen activator (HEPA) referred to above, the enzymes of the invention have a different molecular weight and amino acid composition (see Table 3). Also, the enzyme derived from GPK at least has been found to be fibrinolytic in its own right (i.e. by direct enzymatic action on fibrin, and not only through release of plasmin, see FIG. 4).

The production of enzymes according to the invention and their characterization will now be described in more details by way of example.

CELLS USED IN THE TISSUE CULTURES

Cells of deposited cell line BEB and GPK were used in the following procedures:

(a) Methods of Routine Cultivation

Cells are routinely maintained on a weekly subculturing regime. When just sub-confluent, the cells are detached by exposure to 10% trypsin in dextrose-salt solution for about 2–3 minutes, transferred to a centrifuge tube with about 2 ml of growth medium and spun at 800 rpm for four minutes. The cell pellet is then resuspended in 1 ml of growth medium, a 20 µl aliquot is counted by Coulter Counter, and the cells seeded into clean sterile culture flasks containing growth medium and left in the $CO_2$ incubator at 37° C. for one week as the stock line. The normal seeding density for GPK cells is $10^3$ c/ml. Checks for contamination were made by autoradiography (BEB passage 19, and GPK passages 34 and 50). Cells were seeded onto slides and labelled for five hours with $^3H$ Thymidine, final concentration 1.0 µCi/ml. After coating with Ilford K2 emulsion in gel form, the slides were kept at 4° C. for one week, developed and stained with Giemsa stain and examined for their nuclear label and any cytoplasmic or non-cellular labelling. Both lines showed only the normal nuclear label. Mycoplasma contamination was also excluded by broth culture (BEB, 17, and GPK passage 7). The passages used for enzyme collections were GPK (33–53) and BEB (19–27).

(b) Liquid Nitrogen Storage

After the trypsinising and counting procedure described above the cells are spun down and the cell pellet resuspended in growth medium containing 7.5% dimethyl sulphoxide (DMSO) to give a cell concentration of about $2 \times 10^6$ cells/ml. The cell suspension is placed in ampoules in a polystyrene box which is cooled stepwise as follows: 3 hours at $+4°$ C., 30 minutes at $-18°$ C., overnight at $-70°$ C., and then transferred to the nitrogen refrigerator.

(c) Reconstitution after Liquid Nitrogen Storage

Ampoules containing cells to be reconstituted are removed from the nitrogen and allowed to thaw rapidly in a beaker of warm water (35° C.). The cells are then transferred to a culture flask containing 10 ml of growth medium and left overnight at 37° C. The medium is changed the following day to remove DMSO.

(d) Scale-up in Culture Size

Enzyme yields per cell are extremely small (0.1 pg/cell) thus the need for using large-scale culture systems to support high concentrations of cells in a unit scale-up process system (as opposed to multiples of small scale apparatus). It is also important that the culture system will produce as concentrated a product as possible to facilitate the purification procedure. The following culture systems have been used to scale-up cell and enzyme production from 25 and 75 cm² flasks:

(i) Roller culture Polystyrene and glass bottles of various sizes are rolled slowly (12 rph) using standard tissue culture roller apparatus. Productivity is increased because the whole internal surface area is utilised rather than just one surface. More concentrated yields of enzyme are produced because the cell to medium ratio can be increased compared to stationary cultures.

(ii) Stack plate cultures The culture surface is a series of flat, circular stainless steel discs mounted horizontally on a stirrer shaft 2–4 mm apart. The whole assembly is placed in a fermenter vessel and slowly stirred (up to 100 rpm). The culture size varies from 5 liters (12,200 cm²) to 210 liters (330,000 cm²) of culture area and although allowing a larger increase in cell capacity in a single unit does not permit a more concentrated product formation.

(iii) Microcarrier cultures Microcarriers are small spheres which permit cell growth over their surface and can be kept stirred in suspension. This allows the use of large-scale fermentation equipment, normally available for suspension cells only, to be used for cells that grow attached to a substrate. The advantages of this system are full environmental control to keep the culture homogeneous and in an optimum environment, unlimited scale-up potential, and easily changeable cell to medium ratios to allow more concentrated product formation. Typically microcarriers provide 5000 cm² culture area per gram and are used at concentrations between 3 and 15 g/liter depending upon the sophistication of the culture apparatus.

The principles of cell cultivation are the same for all types and scale of culture vessel.

EXAMPLE (a) Harvesting of GPK Cell-Derived Enzyme (CDE) from a Microcarrier Culture Cytodex-3 (Pharmacia Fine Chemicals) was the microcarrier used at a concentration of 10 g/liter. The culture apparatus was a 5 liter Biocul Fermenter (L. H. Fermentation Ltd) with a working capacity of 4.5 liters, attached to a perfusion resevoir containing 2 liters of medium. The surface area to medium ratio is over 4 times higher than that in roller bottles using this level of microcarrier and the cells can only be kept viable and active by means of critical control over oxygen, pH and nutrient concentrations and fast perfusion rates. The culture apparatus that meets these requirements has been described (Griffiths, J. B. and Thornton, B., J. Chem. Tech. Biotechnol. 1982, 32, 324–329)

The cell seed of $2.5 \times 10^9$ cells was prepared in roller bottle culture and added to the culture containing Eagles (MEM) growth medium supplemented with 10% FBS, 0.001% Tween 80 and Hepes buffer. After 72–96 hours growth at 37° C. the cells grow sufficiently to cover about 70% of the available substrate (typically about $1.4 \times 10^{10}$ cells). The medium is decanted, the cells plus microcarriers are washed twice with a serum-free medium, and then topped up with serum-free MEM.

Incubation at 37° C. then continues for at least 60 hours to allow further cell growth and enzyme secretion to occur.

At the end of the incubation the supernatant is poured off and spun at 450 g for 10 minutes to remove any cells in suspension. The supernatant is then spun at 40,000 g for 30 minutes at 5° C. A 50 μl aliquot is removed for fibrin plate assay, the supernatant is freeze-dried and transferred to a weighed bottle and stored in the liquid nitrogen refrigerator. Alternatively the supernatant may be concentrated by ultrafiltration.

(b) Purification of GPK Cell Culture Supernatant

Figure 1:
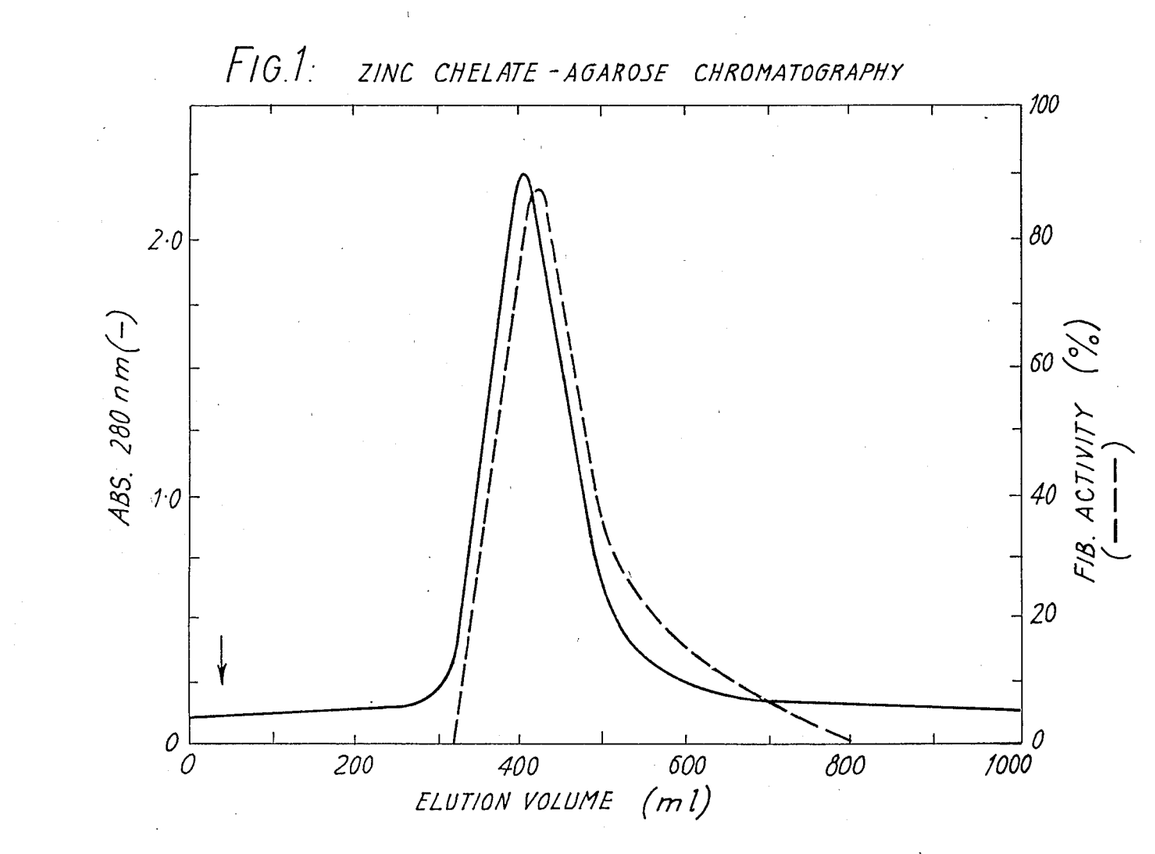

The concentrated culture supernatant was partially purified by chromatography on a column of zinc chelate agarose (4.4 cm × 12 cm) previously equilibrated at 4° C. with 0.02M Tris-HCl, pH 7.5 containing 1M NaCl and 0.01% Tween 80. 5 liter of conditioned medium was applied to this column at a flow rate of 120 ml/hour. After washing the column with 2 liter of equilibration buffer, the bound proteins were eluted with a linear gradient from 0 to 0.05M imidazole (total volume 1 liter) in the equilibration buffer. The eluate was collected in 8 ml fractions. The ultraviolet (UV) absorbance of each fraction was monitored at 280 nm and the fibrinolytic activity was assessed by fibrin plate assay (FIG. 1). The active fractions were combined and its specific activity determined by fibrin clot lysis time method.

Figure 2:
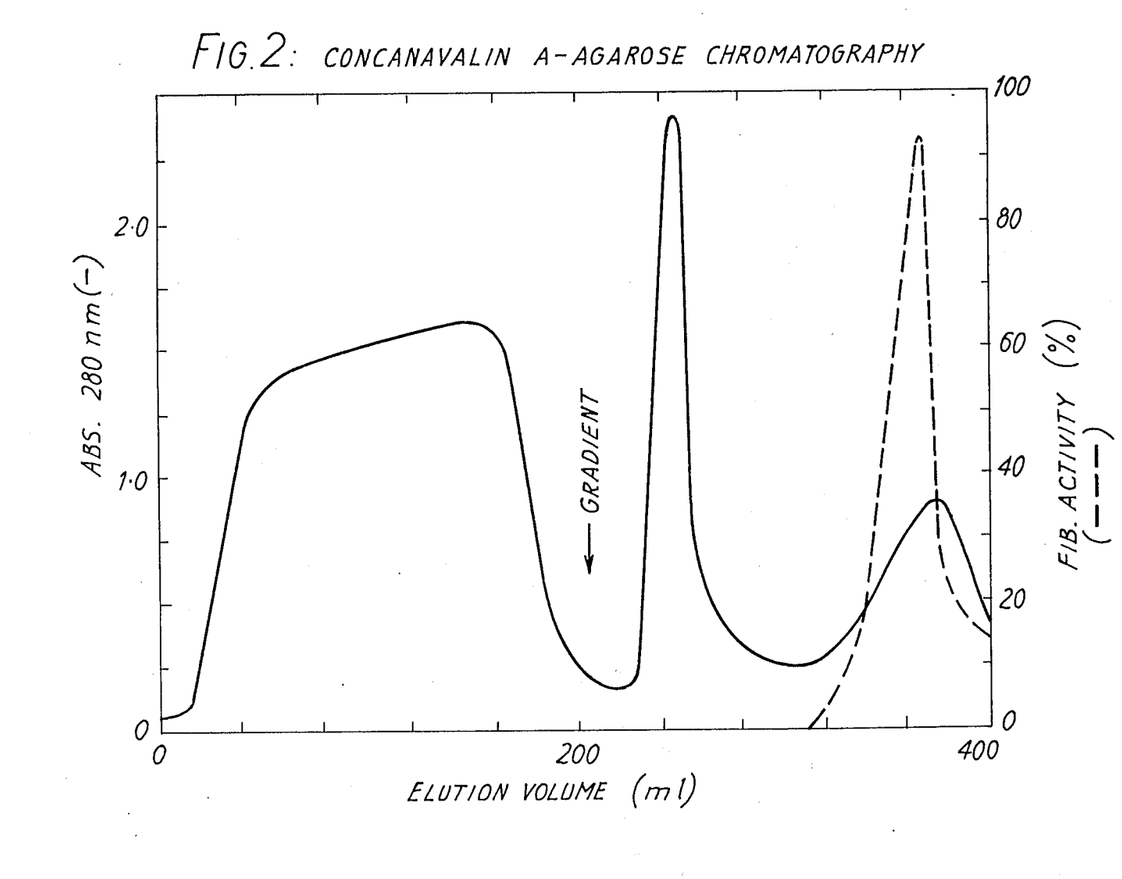

In the next step, the pooled fractions were applied to a concanavalin A-agarose column (2.2 × 15 cm) equilibrated with 0.01M sodium phosphate buffer, pH 7.5 containing 1M NaCl and 0.01% Tween 80. The column was washed with the equilibration buffer at a flow rate of 10 ml/hour until the UV absorbance at 280 nm of the eluate was below 0.15. A linear gradient of the equilibration buffer (200 ml) to 0.01M sodium phosphate buffer, pH 7.5 containing 0.6M α-D-methylmannoside, 2M KSCN and 0.01% Tween 80 was applied to elute the absorbed material. Fractions of 5 ml were collected for measurement of UV absorbance and fibrinolytic activity as described earlier (FIG. 2). The active fractions were pooled and KSCN concentration was increased to 1.6M adding solid KSCN to the pooled fractions. The solution was then concentrated by dialysis against solid polyethylene glycol mol. weight 15,000–20,000 daltons.

Figure 3:
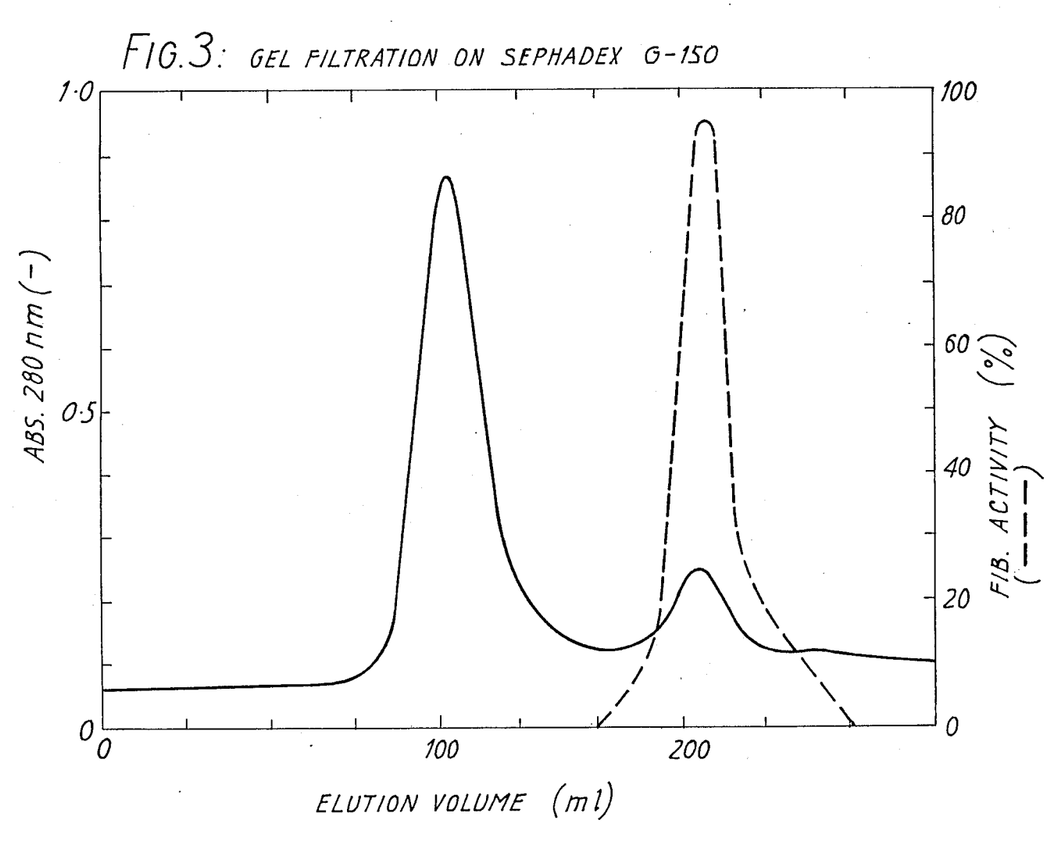

The concentrated solution (5–8 ml) was centrifuged and gel filtered on a Sephadex G150 (superfine) column (2.5 × 90 cm) in 0.01M sodium phosphate buffer, pH 7.5 containing 1.6M KSCN and 0.01% Tween 80. Fractions of 3 ml were collected at a flow rate of 9 ml/hour. The active enzyme eluted as a single peak which conincided with a small protein peak (FIG. 3). Fractions containing active enzyme were pooled, concentrated by dialysis against polyethylene glycol and stored at −80° C.

Alternatively, the eluate from concanavalin-A-agarose column may be further purified by affinity chromatography on lysine-Sepharose or fibrin-Sepharose. The results of the purification of the GPK derived enzyme are summarized in Table 1.

(c) Enzyme Assay (i) Fibrin Plate Assay

Fibrin plates were prepared as follows. In a 52 mm diam. polystyrene Petri dish, 3 ml of 1 mg/ml fibrinogen in Fibrin Plate Buffer was clotted by 10 µl of thrombin (250 units/ml) and allowed to stand for at least 30 minutes at room temperature. 50 µl of supernatant was applied in duplicate on one plate together with 50 µl of plasmin standard (10 µl/ml) and the plate incubated for 20 hours at 37° C. The area of lysis was measured by orthogonal diameters and expressed as "plasmin units" (1 Pu=lysis produced by 1 ng plasmin).

(ii) Fibrin clot lysis time method

The fibrinolytic activities of GPK and BEB derived enzymes were compared with the activity of a standard urokinase solution (1st International Reference Preparation of human urokinase, established 1966). A standard vial of urokinase was dissolved in 50 mM sodium diethylbarbiturate buffer, pH 7.8 containing 0.1 M NaCl and 0.25% w/v gelatin. Several dilutions of standard urokinase and fibrinolytic enzyme were prepared in the above buffer. All other reagents were diluted in the same buffer and kept on ice before mixing. 0.2 ml of diluted urokinase or enzyme solutions were placed into a series of $10 \times 50$ mm tubes. This was followed by 0.05 ml human plasminogen (3 mg/ml), 0.5 ml human fibrinogen (0.25%, w/v) and 0.05 ml thrombin (40 NIH units/ml). The contents were mixed quickly and the tubes were placed in a 37.5° C. water bath. A stopwatch was started immediately and the end point of the lysis time recorded by gently tilting the tube. A calibration graph was prepared by plotting log lysis time (in min.) against log urokinase concentration in the clot. The dilution factor of the enzyme solution giving the same lysis time as the urokinase standard solution of 0.5 IU/ml was taken for calculation of the activity of the non-diluted enzyme solution. The fibrinolytic activity of the enzyme was therefore expressed in International Units (IU).

The average specific activity (fibrinolytic activity/mg of protein) of GPK-derived purified enzyme was approx. 12,500 IU/mg.

(d) Protein Estimation

Protein concentration was measured by the improved Coomassie Blue G dye binding assay of Read & Northcote (Anal. Biochem. 116, 53–64, 1981) using bovine serum albumin, fraction V, as a standard.

(e) Controls

One batch of 670 mg of freeze-dried material was prepared in the manner described in (a) above but without cells present. This material gave a negative result on a fibrin plate analysis. The supernatants from several other cell lines were also examined for fibrinolytic activity but were either negative, or showed only traces of fibrinolytic action. The results appear below in Table 2.

(f) Effect of Heating(Enzyme Inactivation)

Before freeze-drying a batch of cell derived material (GPK 37, batch 3), two 0.5 ml aliquots were removed. One was heated in a boiling water bath for five minutes, the other was used as the normal control. On the fibrin plate assay the boiled sample was inactive.

PHYSIOCHEMICAL PROPERTIES (a) Fibrin Plate Assay

The fibrinolytic activities of GPK derived enzyme solutions were determined on plasminogen-containing bovine fibrin plates. 3 ml of fibrinogen solution (ex-Sigma, 1 mg/ml) was clotted in a petri dish (Gibco Europe Ltd.) 52 mm diameter, by the addition of 2.5 units of thrombin in 10 µl buffer. The plates were allowed to stand at room temperature for at least 30 min before being used. 50 µl volumes of the test samples were applied to the plates which were then incubated for 18 hours at 37° C. The zone of lysis was measured and expressed as a percentage of total lysed area caused by plasmin (10 µg/ml).

(b) Pre-Treatment of Fibrin Plates

To inactivate the inherent plasminogen content of the fibrin layer, the fibrin plates were heated at 80° C. for 45 min. They were then allowed to cool to room temperature before being used. Care was taken not to allow the condensation to develop on the surface of the fibrin layer.

This procedure resulted in denaturation of the contaminating plasminogen and abolished the susceptibility of the plates to the action of plasminogen activators, such as urokinase, (and also reduced the sensitivity of the plates to proteolysis).

Figure 4:
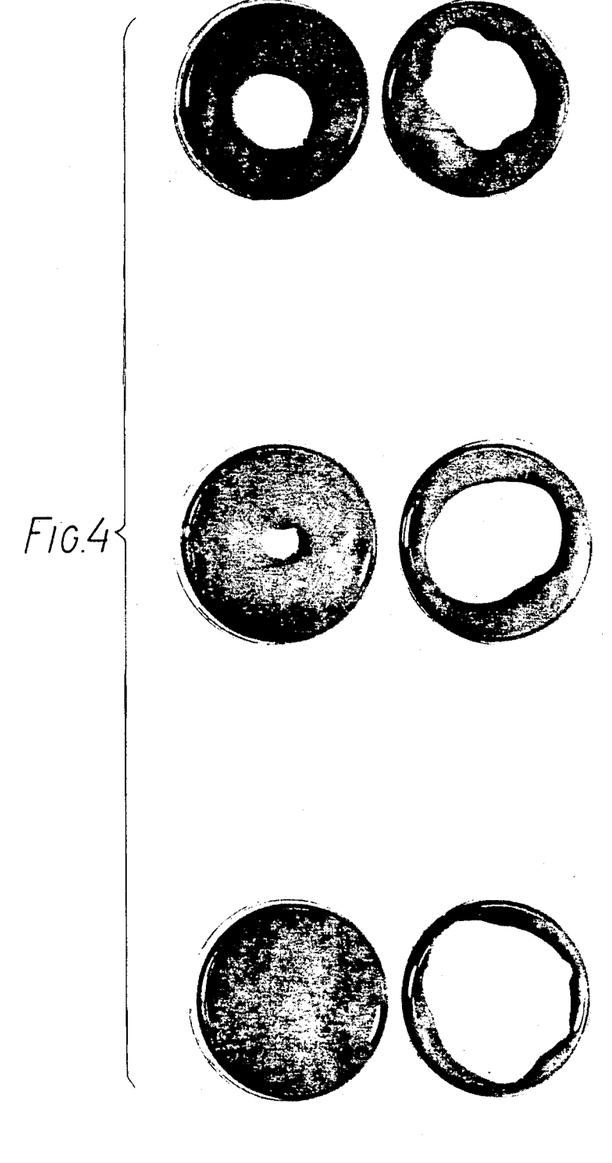

The results are shown in FIG. 4 from which a comparison may be made of the fibrinolytic activity of the GPK derived enzyme with that of plasmin and urokinase on heated and unheated fibrin plates. As expected, in the case of urokinase, there was no fibrinolytic activity on the heated plate due to the inactivation of contaminant plasminogen.

However, GPK derived enzyme was still able to lyse the fibrin layer on the heated plate, although to a lesser extent than the lysis on a plate which had not been heated. These results indicate, that unlike known plasminogen activators, GPK-derived enzyme possesses both direct fibrinolytic and plasminogen activator activity.

Fibrinolytic activity of GPK derived enzyme was also tested on plasminogen-free fibrin plates prepared from commercially available plasminogen-free fibrinogen, and was found to be lytic. Urokinase was negative in this test and did not lyse plasminogen-free fibrin plates.

(c) Estimation of Molecular Weight

The molecular weight of GPK derived enzyme was determined on 10% polyacrylamide slab gel in sodium dodecyl sulphate under reducing and non-reducing conditions according to the method of Laemmli (1973). (Laemmli, U. K. and Favre, M., J. Mol. Biol. 80, 575–599 (1973)).

Samples were heated at 90° C. for 5 min prior to electrophoresis and the following reference proteins were used as standards. Phosphorylase b (92,500), bovine serum albumin (67,000), ovalbumin (45,000), carbonic anhydrase (31,000), soyabean trypsin inhibitor (21,500) and lysozyme (14,400).

A densitometric trace of the gel slab resulting from one experiment was used for the calculation of molecular weight. The distance by which GPK derived enzyme had migrated was recorded on a standard curve obtained by plotting the relative migration of the reference proteins against their log molecular weights.

The results show that the molecular weight of the purified GPK derived enzyme was approximately 56,000±2000 under non-reducing conditions and 62,000±3000 under reducing conditions (by addition of 2 mercaptoethanol) infering the presence of disulphide bridges in the enzyme molecule. The molecular weight is in close agreement with the approximate molecular weight of 65,000±3000 estimated by gel filtration on a Sephadex G150 column. Similar results were obtained for the BEB derived enzyme.

(d) Isoelectric Focussing

Isoelectric focussing was carried out in thin layer LKB Ampholine polyacrylamide gel plates in the pH range 3.5-9.5 using an LKB Multiphor unit. 20 μl aliquot of GPK enzyme was applied to the gel. Focussing was carried out at constant power of 8 W with an initial current of 20 mA and a voltage maximum of 1.1 KV. The focussing temperature was 10° C. and the running time was 90 min.

The pH gradient across the gel was measured at room temperature at 0.5 cm intervals using a miniature combination surface electrode (Pye-Ingold type 403-30-M3) with a 3 mm diameter tip and a pH meter (Corning model 7030). The gel was stained for protein using Coomassie brilliant blue R-250 (Sigma Chemical Co.) after fixing in 10% trichloracetic acid (TCA) solution.

Figure 5:
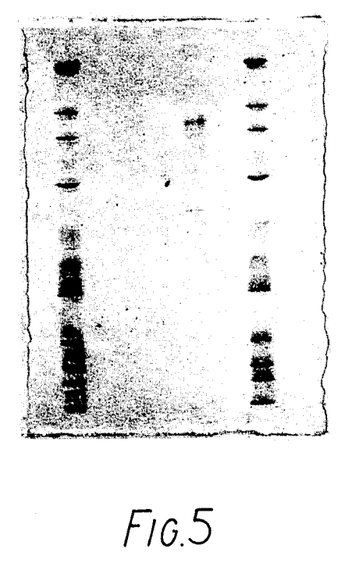

The results obtained are shown in FIG. 5. The isoelectric points (pI) of the purified GPK and BEB derived enzymes were found to be 4.6.

(e) Amino Acid Composition

The amino acid compositions of GPK and BEB enzymes were determined with a Locarte amino acid analyser after hydrolysis of the protein sample with constant boiling 6M HCl (Aristar) in vacuo at 110° C. for 20 hours.

The amino acid compositions of the enzymes are shown in Table 3. For comparison, the composition of the plasminogen activator derived from human malignant melanoma (HEPA) is also included in the table. (Rijken, D. C. and Collen, D., J. Biol. Chem. 256, 7035–7041 (1981)).

It can be seen that the GPK and BEB enzymes are basically similar in composition, but with the minor differences which would be expected between two different cell lines. Both GPK and BEB have a different amino-acid composition from that published for HEPA.

(f) Kinetic Studies

The amidolytic activity of the GPK derived enzyme was determined using various chromogenic substrates. The activity was measured spectrophotometrically in a 1 cm path length cuvette at 37° C. with a Gilford system 2600 spectrophotometer linked to a Hewlett Packard 7225A Graphics Plotter. Z The partially purified enzyme was incubated with varying concentrations of each of the chromogenic substrates in 0.05M Tris-HCl buffer at the pH and ionic strength indicated in Table 4, which shows the values of the kinetic parameters obtained for the GPK derived enzyme with various substrates. The initial release of p-nitroaniline was monitored at 405 nm. A molar extinction coefficient of 10,500 liter mol$^{-1}$ cm$^{-1}$ was used for p-nitroaniline.

(g) Fibrin Binding Studies

The absorption of GPK and BEB derived enzymes to fibrin clots was determined by mixing 1 ml plasminogen-free fibrinogen (1.5 mg/ml), 25 μl GPK or BEB (25 μg/ml) and 50 μl thrombin (20 NIH U/ml). The above mixtures were made up in 0.05M sodium diethylbarbiturate buffer, pH 7.8 containing 0.1M NaCl and incubated at 37° C. for 30 min. The clots were recovered by centrifugation, washed with buffer and then extracted with 1 ml of 0.05M sodium diethylbarbiturate buffer, pH 7.8 containing 1M KSCN. Aliquots of clot supernatants and clot extracts were tested on plasminogen-containing fibrin plates.

The results show that most of the added enyme was bound to fibrin clots with little or no active enzyme remaining in the supernatant. However, similar experiments with urokinase showed that there was insignificant binding to fibrin clot.

(h) Binding of GPK derived enzyme to an experimental thrombus in artificial circulating system The ability of GPK-derived enzyme to bind to whole blood clot was examined in an in vitro Chandler loop circulating system. An experimental cross-linked thrombus was produced in a polyethelene tube of 3 mm internal diameter (prewashed with 0.01% Tween) by mixing citrated whole human blood (1 ml) with 50 μl of 0.05 M CaCl$_2$ and 25 μl of thrombin (100 NIH U/ml). After incubation at 37° C. for 1 hour, on a turntable (30 rpm), the thrombus was poured into a Petri dish and washed twice with 0.05M sodium diethylbarbiturate buffer, pH 7.8 containing 0.25% w/v gelatin and 0.1M NaCl. The thrombus was then aspirated back into the tube together with 0.9 ml of autologous plasma or buffer. 100 μl of GPK derived enzyme (approx 500 IU) was added, the loop was placed back on the turntable and incubated for further 2 hours at 37° C. The clots were removed, washed with buffer as before and then extracted with 1 ml of 0.05M diethylbarbiturate buffer, pH 7.8 containing 1M KSCN for 1 hour at 4° C. 50 μl aliquots of the clot extract and of the clot supernatant from the tube were applied to plasminogen containing fibrin plates and incubated for 18 hours at 37° C.

The results obtained show that the fibrinolytic activity of the clot extract, and hence the amount of bound enzyme, was significantly higher than the clot supernatant. Similar results were obtained when the experiment was repeated with Indium$^{111}$-labelled enzyme.

In view of these results, the radiolabelled enzyme could be used diagnostically as an efficient means of in vivo thrombus localisation.

(i) Immunodiffusion Analysis

Antisera against GPK and BEB derived material and human urokinase were raised in rabbit according to the method described by Rijken & Collen (J. Biol. Chem. 256, 13, 7035–7041, 1981). The IgG fractions of the antisera were isolated by affinity chromatography on Protein-A-Sepharose column.

Double immunodiffusion analysis was carried out in 1.5% agar gels according to the technique of Ouchterlong and Nilsson (Handbook of Experimental Immunology, 2nd Edition, chap. 19, Blackwell, Oxford). Samples were added to the punched well and allowed to diffuse overnight at 4° C. in a humid atmosphere.

The results indicate that GPK and BEB derived enzymes are immunologically similar and that rabbit anti- GPK IgG and anti-BEB IgG did not react with urokinase. Similarly, neither enzyme cross-reacted to antibodies against urokinase.

(j) Inhibition of GPK-dervied enzyme activity by 2-mercaptoethanol

Various dilutions of the stock solution of 2-mercaptoethanol were prepared in 0.05M sodium diethylbarbiturate buffer, pH 7.8 containing 0.01% Tween 80. GPK derived enzyme (25 μg/ml) was mixed with an equal volume of diluted 2-mercaptoethanol solution and the mixture incubated at 37° C. Control sample contained enzyme with an equal volume of buffer. After 15 min, 50 μl aliquot of the mixture was applied to plasminogen containing fibrin plate to assess the residual enzyme activity. The enzyme activity was also quantitated by fibrin clot lysis time method.

The results obtained indicate that a significant proportion (>80%) of the enzyme activity was inhibited by incubation with 2-mercaptoethanol at a concentration of 10 mM or above. These results, together with those obtained during molecular weight estimation, indicate that the intramolecular disulphide bridges are essential for enzyme activity.

(k) Effect of Poly-D-lysine on GPK derived enzyme activity

The effect of Poly-D-lysine on the plasminogen activator activity of the partially purified GPK derived enzyme was investigated, essentially according to the method of Allen (Thromb. Haemostas. (Stuttgart) 47, 41–45, 1982). The reaction mixture consisted of 400 μl of 0.05M Tris-HCl buffer, pH 7.5, 25 μl Tween 80 (0.4%), 125 μl plasminogen (200 μg/ml), 200 μl chromogenic substrate S-2251 (3.5 mM), and 50 μl of poly-D-lysine (5 μg/ml) or water control. The reaction was started by addition of 200 μl of enzyme and the change in optical density at 405 nm was monitored at 37° C. for 20 min.

It was found that, in the absence of poly-D-lysine, a parabolic curve was obtained similar to the one obtained with urokinase in the presence of poly-D-lysine under these conditions. However, when poly-D-lysine was added to the reaction mixture containing GPK derived enzyme, the solution turned turbid giving rise to a complex change in optical density with time. These preliminary results suggest that poly-D-lysine interacts with the GPK derived enzyme in a manner different to that with urokinase.

It will be appreciated from the above description that the enzymes of the invention have utility for therapeutic, prophylatic and diagnostic purposes. For therapeutic and prophylatic use the enzymes may be formulated into pharmaceutical compositions, particularly each compositions which are suitable for parenteral administration. Thus the compositions may comprise any conventional parenteral carrier such as sterile, pyrogen free physiological saline. For human administration, a suitable dosage rate is from about 10 mg to about 80 mg per 24 hour period, preferably in 2 or 3 doses by intravenous administration.

For diagnostic purposes the enzymes may be radioactively labelled by conventional labelling techniques for example with $I^{125}$ or $In^{111}$. The radioactively labelled enzyme may then be introduced into a vascular system to be investigated and sites of increased radioactivity sought.

TABLE 1

PURIFICATION OF GPK-DERIVED ENZYME

|  | Volume (ml) | Total Protein (mg) | Total Activity (IU) | Specific Activity (IU/mg) | Yield (%) | Purification Factor |
|---|---|---|---|---|---|---|
| Conditioned medium | 5,000 | 1,606 | 57,800 | 36 | 100 | 1 |
| Zinc chelate-agarose | 80 | 205 | 54,100 | 264 | 93 | 7.3 |
| Concanavalin-A-agarose | 72 | 11 | 38,100 | 3,464 | 66 | 96 |
| Sephadex G-150 | 27 | 2 | 25,000 | 12,500 | 43 | 347 |

TABLE 2

FIBRINOLYSIS BY CELL LINES

|  |  | FIBRINOLYTIC INDEX ± S.D. expressed as Plasmin Units | |
|---|---|---|---|
| CELLS | | SUPER- | CELL |
| Designation | Origin | NATANT | EXTRACT |
| GPK | CNCMI-222 | 643 ± 101 | 787 ± 69 |
| BEB | CNCMI-221 | 376 ± 43 | N.D |
| HeLa | Human cervical carcinoma | Nil | 34 ± 8 |
| MRC5 | Human lung fibroblasts | Nil | 30 ± 8 |
| Swiss 3T3 | Mouse endothelial cells (?) | 17 ± 4 | 153 ± 21 |
| RLCW | Rat liver parenchymal cells | 56 ± 13 | 96 ± 13 |
| FCC | Chimp liver parenchymal cells | Nil | 3 |
| GLV 3 | Green monkey kidney epithelium | Nil | N.D. |
| SV40 3T3 | Virus transformed 3T3 cells | 39 ± 17 | N.D. |

N.D. = Not determined

TABLE 3

AMINO ACID COMPOSITIONS (EXPRESSED AS NUMBER OF RESIDUES PERCENT)

| AMINO ACID | MALIGNANT MELANOMA PLASMINOGEN ACTIVATOR (HEPA)* | GPK | BEB |
|---|---|---|---|
| Cysteic acid | N.D.** | | 2.1 |
| AsP | 9.8 | 10.9 | 9.8 |
| Thr | 5.4 | 5.1 | 4.6 |
| Ser | 9.2 | 6.4 | 6.4 |
| Glu | 13.1 | 10.1 | 11.5 |
| Pro | 7.1 | 6.1 | 4.3 |
| Gly | 10.4 | 8.4 | 7.1 |
| Ala | 6.6 | 7.8 | 8.3 |
| Val | 4.1 | 6.0 | 6.7 |
| Met | 0.9 | 2.4 | 1.0 |
| ILeu | 3.0 | 4.8 | 3.5 |
| Leu | 8.1 | 9.7 | 13.9 |
| Tyr | 4.0 | 3.5 | 2.2 |
| Phe | 3.7 | 4.5 | 3.6 |
| His | 3.3 | 2.8 | 2.6 |
| Lys | 5.5 | 6.5 | 7.1 |
| Arg | 5.9 | 4.8 | 5.1 |

*Data from Rijken, C. D. and Collen D., J. Biol. Chem. 256, 7035–7041 (1981)
**N.D. = Not determined

TABLE 4

| Substrate | pH | Ionic Strength I | GPK** Km (M) | GPK** Vmax (M/min/M enzyme) | OTHER ENZYMES* Km (M) | OTHER ENZYMES* Vmax |
|---|---|---|---|---|---|---|
| H—D—Val—Leu—Lys—pNA.2HCl | 7.4 | 0.15 | 10060 | 14.7 | Plasmin 300 | 0.5 M/min/CU |
|  | 7.4 | 0.006 | 14400 | 27 |  |  |
|  | 9.0 | 0.15 | 9561 | 4.08 |  |  |
| H—D—Ile—Pro—Arg—pNA.2HCl | 8.4 | 0.15 | 715 | 2.581 | Urokinase 200 / Plasmin 9000 | $2 \times 10^{-4}$ M/min/U / 5 m/min/U |
|  | 8.4 | 0.004 | 715 | 2.581 | Thrombin 3 | 0.1 M/min/U |
| Glu—Glu—Arg—pNA.HCl | 8.8 | 0.0037 | 1282 | 5.36 | Urokinase 90 | $3.1 \times 10^{-4}$ M/min/PLOUG.U |
| Benzoyl-Val—Gly—Arg—pNA.HCl | 9.0 | 0.05 | 839.8 | 1.1 | Melanoma 1000 | 0.53 M/min/IU |
|  |  | 0.0035 | 557.76 | 1.4 (substrate concentration by extinction) |  |  |
|  |  | 0.0035 | 400 | 1.387 (substrate concentration by weight) |  |  |
| Benzoyl-Phe—Val—Arg—pNa.HCl |  | 0.15 |  |  | Thrombin 110 | 0.036 M/min/NIH.U |

*Values quoted in literature
**Values obtained with partially purified enzyme

We claim:

1. A method of producing an enzyme having fibrinolytic activity per se or activity as a plasminogen activator which comprises culturing cells of an established cell line of non-cancerous epithelial cells designated GPK (CNCMI-222) or an established cell line of non-cancerous epithelial cells designated BEB (CNCMI-221) and isolating an enzyme-containing fraction from the culture.

2. A method according to claim 1 wherein the enzyme-containing fraction is obtained by collecting a supernatant fraction containing the enzyme.

3. A method according to claim 1 wherein the enzyme-containing fraction is obtained by extracting an enzyme-containing fraction from the cells.

4. A method according to claim 1 wherein the cells are grown on a serum-containing medium, the serum-containing medium is replaced by a serum-free medium and the enzyme is recovered from a supernatant fraction comprising said serum-free medium, or extracted directly from the cells.

* * * * *